United States Patent [19]
Dyke et al.

[11] Patent Number: 5,736,355
[45] Date of Patent: Apr. 7, 1998

[54] SELF CONTAINED BIOLOGICAL INDICATOR

[75] Inventors: Denis G. Dyke, Lake Bluff, Ill.; Paul S. Malchesky, Painesville Twp., Ohio; Raymond C. Kralovic, Willoughby, Ohio; Donna M. Richardson, Bratenahl, Ohio; Joseph J. Switka, Willoughby, Ohio

[73] Assignee: Steris Corporation, Mentor, Ohio

[21] Appl. No.: 645,259

[22] Filed: May 13, 1996

[51] Int. Cl.[6] .............................. C12Q 1/22; C12M 1/34
[52] U.S. Cl. ..................... 435/31; 435/287.4; 435/287.6; 435/288.2
[58] Field of Search ........................ 435/31, 287.4, 435/287.6, 287.7, 287.9, 288.1, 288.2

[56] References Cited

U.S. PATENT DOCUMENTS

| | | |
|---|---|---|
| 2,854,384 | 9/1958 | Beakley et al. . |
| 3,134,725 | 5/1964 | Brook et al. . |
| 3,239,429 | 3/1966 | Menolasino et al. . |
| 3,255,926 | 6/1966 | Modderno . |
| 3,378,168 | 4/1968 | Hildebrandt . |
| 3,440,144 | 4/1969 | Andersen . |
| 3,585,112 | 6/1971 | Ernst . |
| 3,613,955 | 10/1971 | Wetherell, Jr. . |
| 3,616,263 | 10/1971 | Anandam . |
| 3,657,073 | 4/1972 | Burton et al. . |
| 3,752,743 | 8/1973 | Henshilwood . |
| 3,762,540 | 10/1973 | Baumann et al. . |
| 3,875,012 | 4/1975 | Dorn et al. . |
| 3,968,872 | 7/1976 | Cavazza . |
| 4,136,775 | 1/1979 | Zaltsman . |
| 4,252,904 | 2/1981 | Nelson et al. . |
| 4,291,122 | 9/1981 | Orelski ..................... 435/288.1 |
| 4,596,773 | 6/1986 | Wheeler, Jr. ............... 435/287.4 |
| 4,885,253 | 12/1989 | Kralovic ................... 435/287.4 |
| 4,937,115 | 6/1990 | Leatherman ............... 428/36.4 |
| 5,500,184 | 3/1996 | Palmer .................... 435/287.4 |
| 5,516,648 | 5/1996 | Malchesky et al. ............ 435/31 |

FOREIGN PATENT DOCUMENTS

| | | | |
|---|---|---|---|
| 37 05 596 | 9/1988 | Germany | ............... 435/287.4 |
| 95/01451 | 1/1995 | WIPO . | |

Primary Examiner—William H. Beisner
Attorney, Agent, or Firm—Fay, Sharpe, Beall, Fagan, Minnich & McKee

[57] ABSTRACT

A self contained biological indicator (A) determines an effectiveness of a microbial decontamination process. A dart (68) has a seal (80) engaged by rim (58) in detents (50C) in fins (36A–36F) of a cap (C). The dart has a cutting edge (76) aligned just above a foil seal (86) sealing a growth medium (F) in a medium housing (D). The dart has a chamber (72) in which challenge spores or other microorganisms on a paper disk (74) are housed. A microporous membrane (G) traps the challenge spores in the chamber while allowing a microbial decontamination fluid to flow through to contact the spores. The housing is lodged by a flange (56) in detents (50A) in fins (36A–36F). After the microbial decontamination process is complete, the cap is forced toward medium housing causing the rim and the flange to dislodge from their respective detents and lodge in detents (50B) resulting in the puncturing of the foil seal, the sealing of the dart within the medium housing and the immersion of the dart and the challenge spores into the growth medium.

14 Claims, 9 Drawing Sheets

5,736,355

SELF CONTAINED BIOLOGICAL INDICATOR

BACKGROUND OF THE INVENTION

The present invention is directed to the art of validating the anti-microbial effectiveness, by checking for completeness of microbial decontamination, i.e. sterilization or disinfection. It finds particular application in conjunction with self-contained biological indicator systems for indicating the effectiveness of an automated liquid sterilization process and will be described with particular reference thereto. However, the invention will also find application in conjunction with gaseous or gas plasma sterilization processes, as well as liquid, gas or other fluid disinfection processes.

Heretofore, various sterilization indicating systems have been provided. The systems generally included a spore carrying element such as a pad. The spore carrying element was mounted in a container. In preparation for use, the spore carrying element was exposed to the environment to be sterilized. A sterilization medium sterilized items in the environment and the spore carrying element. Immediately after the completion of this sterilization process, the spore carrying element was sealed off from the environment, and the spore carrying element was exposed to a culturing medium. After incubation, the cultured medium was examined for evidence of growth of inoculated microorganisms which would indicate that the sterilization process was either complete or unsuccessful.

One concern of the prior art biological indicator systems was that liquid sterilants or disinfectants might dislodge some of the inoculated spores.

A further drawback in some of the prior art systems is the lack of a sufficiently tortuous path to prevent potential recontamination of the inoculated element in the period between microbial decontamination and immersion in the culture medium.

The present invention provides a new and improved self contained biological indicating system which overcomes the above referenced problems and others as will be apparent upon reading and understanding the following summary and detailed description of the embodiments.

SUMMARY OF THE INVENTION

In accordance with one aspect of the present invention, a self contained biological indicator is provided. It is designed to encapsulate the contamination challenging spores on a carrier with a porous membrane. This porous membrane covers the only opening into the spore storage cavity. The sealing of this porous membrane over this opening prohibits the challenge spores from escaping the cavity. However, this porous membrane permits microbial decontaminants to pass through thereby interacting with the challenge spores. The self contained biological indicator also forms a tortuous path between the environment and challenge spores to prevent external recontamination after the internal surfaces and challenge spores have been subject to a microbial decontamination process, such as a sterilization or disinfection process. At the same time, the self contained biological indicator of the present invention permits efficient liquid entrance and exit. After the microbial decontamination process, its effectiveness is determined by puncturing a seal and inserting the spores into a biological growth media where spore viability/destruction is determined after an incubation period.

In accordance with another aspect of the present invention, the self contained biological indicator includes a biological indicator housing assembly containing the spore storage cavity, a cap, and a media housing the combination of which forms a tortuous path between the challenge spores on the internal surfaces of assembly and the environment outside of the cap.

In accordance with a yet more detailed aspect of the present invention, the self contained biological indicator includes a dart defining the spore storage cavity therein. The dart also carries a sealing plug. The cap has a plurality of internal guide fins with detents and a culture medium vial has an outwardly extending flange for engaging the detents. The combination of these parts forms a tortuous path between the challenge spores within the dart and the environment outside of the cap.

One advantage of the present invention is that the tortuous path and porous membrane create a barrier that prevents recontamination of the challenge spores after interaction with the microbial decontaminant.

A second advantage of the present invention is that it prevents challenge spores from escaping the spore storage cavity.

Another advantage that the present invention provides is improved fluid flow access between the challenge spores and the environment.

An additional advantage is that after sterilization, decontamination, or disinfection, the challenge spores are simultaneously immersed and sealed in a growth media without the spores having been exposed to the ambient environment or other sources of potential microbial contamination.

Yet another advantage is that challenge spores are retained on the inoculated carrier to assure a complete population of challenge spores are immersed in the culture medium.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, and steps and arrangements of steps. The specification and drawings are only for the purposes of illustrating a preferred embodiment and not to be construed as limiting the invention.

DETAILED DESCRIPTION OF THE PREFERRED EMBODIMENT

Figure 1:
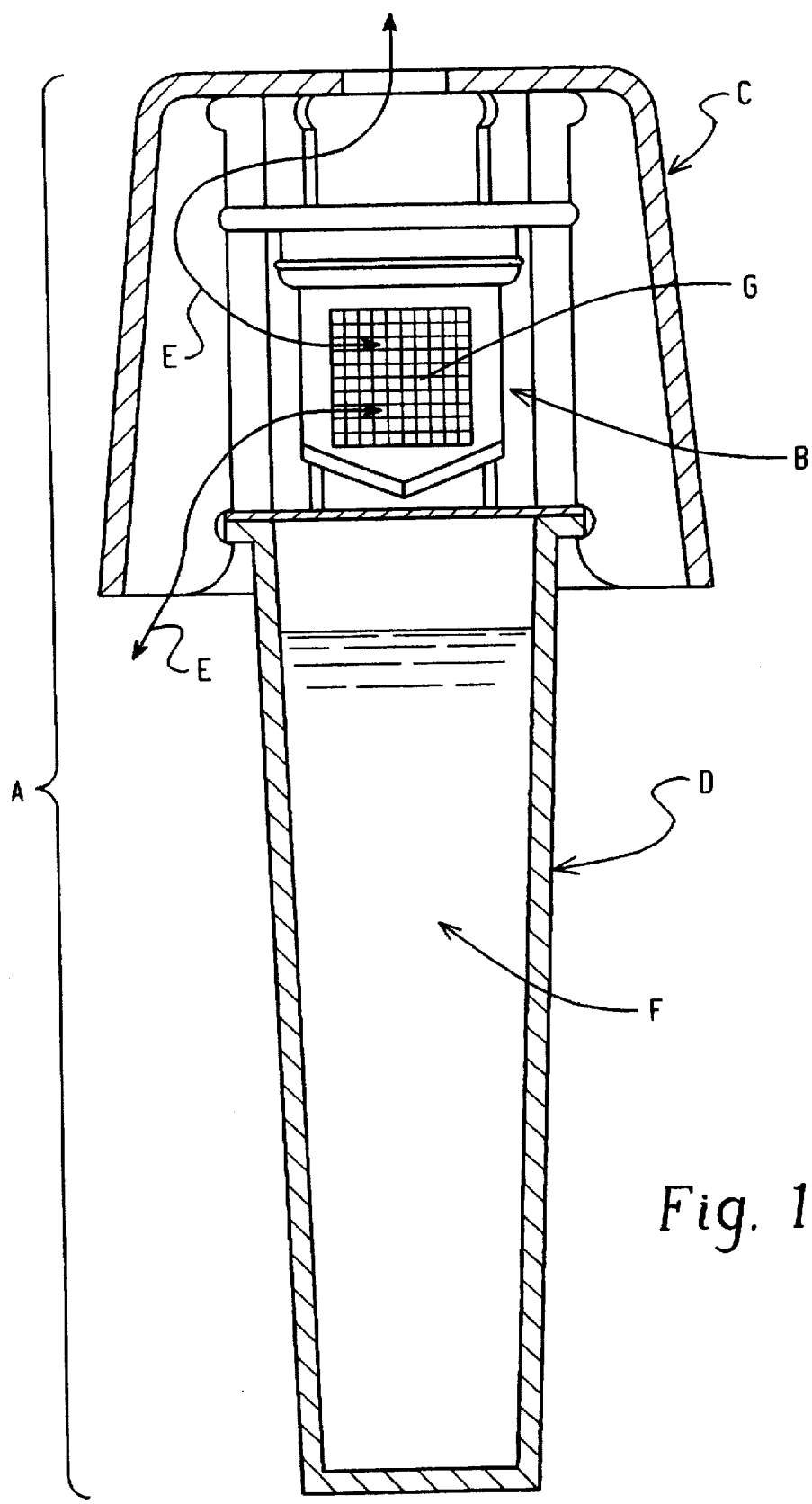
FIG. 1 is a general sectional view taken from the side of a preferred embodiment of the self contained biological indicator with the self contained biological indicator in a first position.

With reference to FIG. 1, a self contained biological indicator A encapsulates challenge spores. The self contained biological indicator A includes a biological indicator housing assembly B, a cap C, and a media housing D.

The cap C substantially envelopes the biological indicator housing assembly B. A tortuous path E is defined by the cap C and the housing D between challenge spores on internal surfaces of the biological indicator housing assembly B, and the environment around the self contained biological indicator A. The cap C is movable with respect to media housing D to open and block the tortuous path E. The cap C further provides indirect fluid access to the biological indicator housing B assembly via the tortuous path E.

The media housing D defines a holding compartment or reservoir for holding a growth media F. The combination of the biological indicator housing assembly B, the cap C, and the media housing D form a mechanism that after a fluid microbial decontamination cycle is simultaneously sealed as the challenge spores are immersed into a growth media F.

The tortuous path E discourages external contamination after the internal surfaces and the challenge spores have been microbially decontaminated. At the same time, the tortuous path E permits efficient entrance and exit of microbial decontamination fluid between the challenge spores and the surrounding environment.

Figure 2:
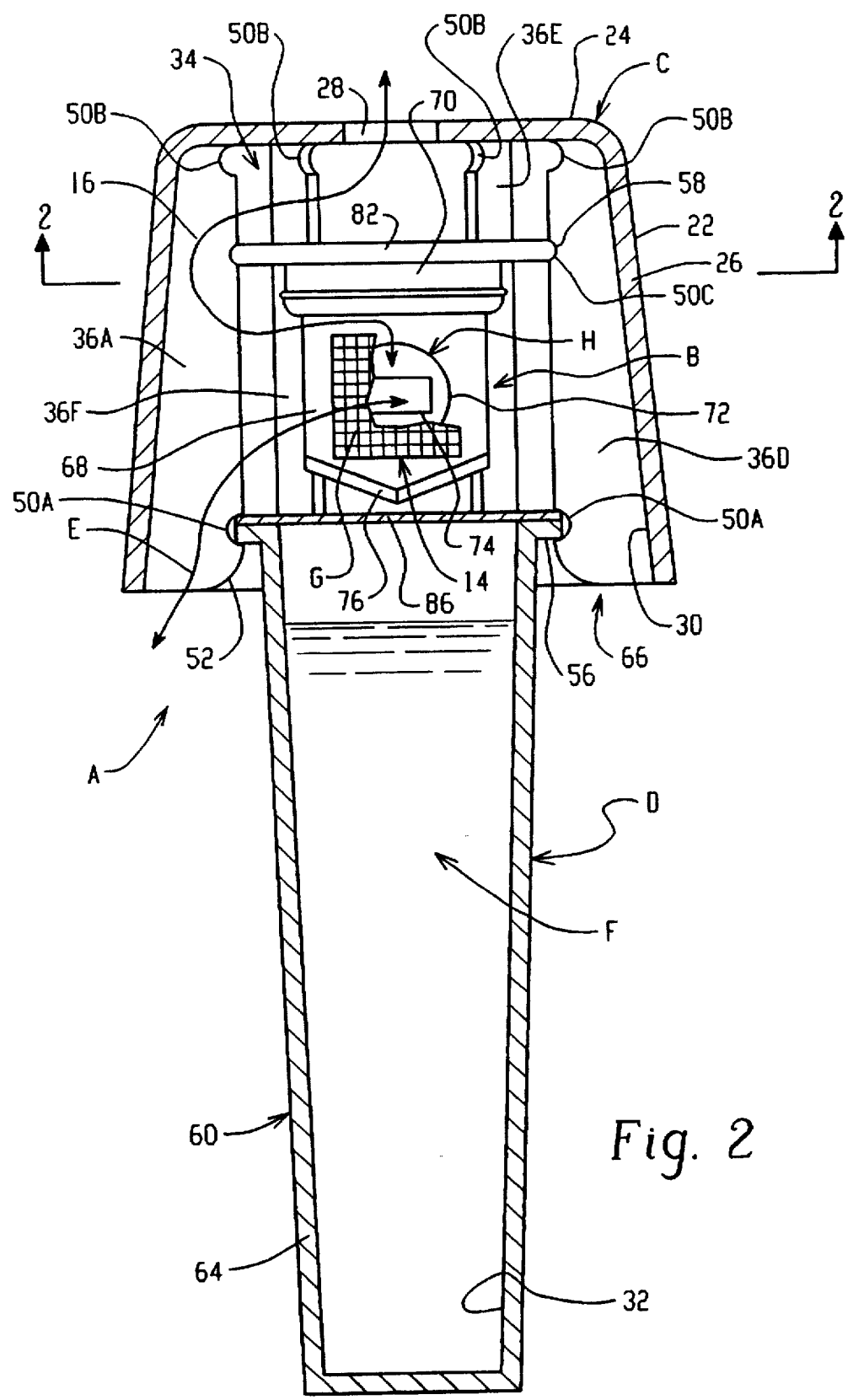
FIG. 2 is a detailed sectional view taken from the side of a preferred embodiment of the self contained biological indicator with the self contained biological indicator in the first position, and with a portion of the microporous membrane removed to expose the spore housing chamber therebehind with a spore impregnated disk therein.

As is described in more detail below, a microporous, preferably hydrophilic, membrane G is positioned within the cap C in the tortuous path E between the environment and the challenge spores. Specifically, the microporous membrane covers and encloses a cavity H (as shown in FIG. 2) within the biological indicator housing assembly B.

This membrane G performs at least three functions. The first function is to prohibit any of the challenge spores from moving out of the biological indicator housing assembly B. The second function is to allow entrance and exit of microbial decontamination fluid and rinsing fluids between the challenge spores and the surrounding environment. This allows the secure storage of encapsulated contamination challenging spores within the biological indicator housing assembly B while testing the effectiveness of a microbial decontamination process, such as a sterilization or a disinfection process. The third function is to permit ready flow of the culture medium to the spores to promote rapid spore growth and detection of any such growth.

The effectiveness of the sterilization process is tested by treating the challenge spores with a microbial decontamination fluid in the same manner as the decontaminated (i.e., sterilized or disinfected) articles. This fluid flows along the tortuous path E to biological indicator housing assembly B where the fluid flows over and among the challenge spores. The media housing D is compressed into the cap C. This compression simultaneously introduces the challenge spores into the growth media and closes off the tortuous path E. This closing off of the tortuous path seals off the challenge spores from the environment.

Figure 2A:
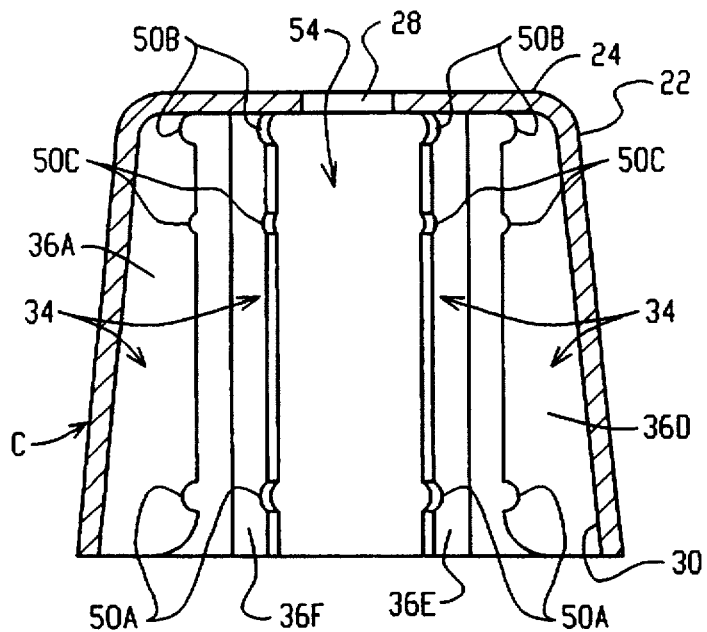
FIG. 2A is an exploded sectional view taken from the side of a preferred embodiment of the self contained biological indicator showing the cap.
Figure 2D:
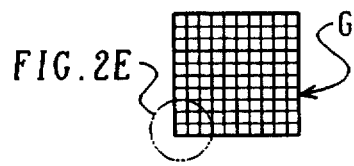
FIG. 2D is the microporous membrane as removed from the dart.
Figure 2B:
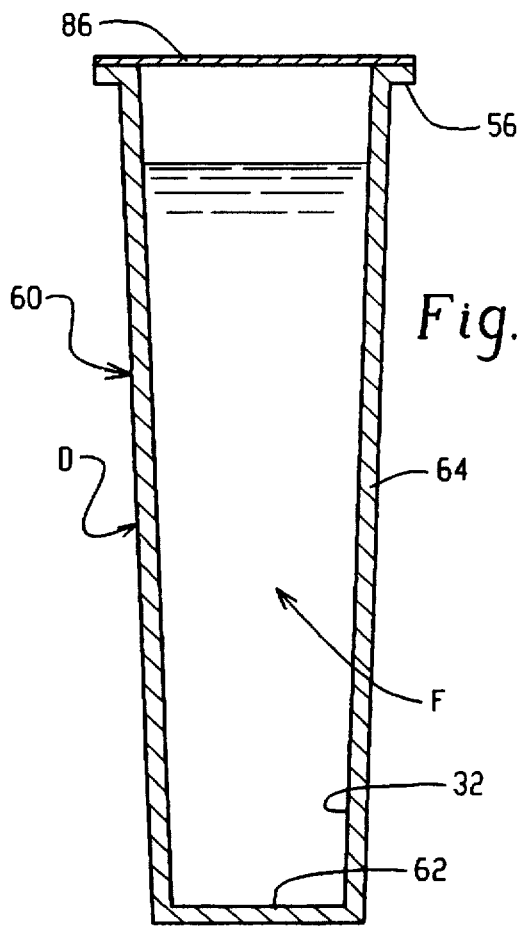
FIG. 2B is an exploded sectional view taken from the side of a preferred embodiment of the self contained biological indicator showing the media vial.
Figure 2E:
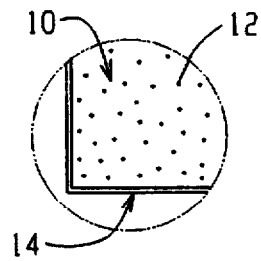
FIG. 2E shows an enlarged piece of the microporous membrane as shown in FIG. 2D.

With reference to the microporous membrane G in FIGS. 1 and 2E, the microporous membrane may be comprised of any suitable natural or synthetic copolymer material which is microporous in nature, and which is or is treated to be hydrophilic. Exemplary of such materials are cellulosic membranes and organic polymer membranes including simple hydrocarbon membranes, such as polyethylene and polypropylene, as well as more polar structures, such as polyamide membranes which includes nylon, acrylic copolymers, polysulfone, polyethersulfone, ethylene vinyl alcohol, and polyacrylonitrile. Other materials that the membrane may be constructed of include polycarbonate, polyphthalate carbonate, and the like.

The membrane material is resistant to degradation by the liquid microbial decontamination solutions and remains porous. The membrane material is resistant to strong oxidants such as peracetic acid, peroxides, hypochlorites, chlorine gas or ions, ethylene oxide gas, and the like. The membrane material is preferably heat insensitive to permit use with high temperature sterilization processes.

With reference to FIG. 2E, the membrane material 10 has micropores 12 of a slightly smaller size than the diameter of the challenge spores or indicator organisms contained within the biological indicator housing assembly B such that the spores cannot escape the assembly B. Due to the porous nature of the membrane G, the decontamination medium, whether gas, gas plasma, steam, or liquid, easily flows through the membrane and contacts the spores or microorganisms. In this regard, it is important when using an aqueous liquid sterilant that the membrane be hydrophilic in nature so that the liquid sterilant solution wets the membrane and is transported through the pore structure of the membrane to the area where the challenge spores are trapped. Of course, if a membrane material is selected which is not normally hydrophilic in nature, i.e., it is hydrophobic, the material may be treated in a manner known to those skilled in the art of using such materials to render the membrane hydrophilic. For instance, a membrane made from polytetrafluoroethylene would have to be treated since polytetrafluoroethylene is naturally hydrophobic. Such treatments include roughening and/or surface treating.

In one embodiment, the microporous membrane is a 0.45 micron pore size membrane that prevents the challenge spores from being washed away by holding them in the biological indicator housing assembly B.

The microporous membrane G is affixed to the biological indicator housing assembly B such that the spores cannot escape the assembly B. To prevent challenge spores from escaping around the microporous membrane, a seal 14 along the edge of the membrane G seals completely around the opening to cavity H in the assembly B. The seal may be formed by heat sealing, thermal fusing ultrasonic welding, microwelding, adhesive bonding, or any other sealing method so long as the seal does not have pores, cracks, holes, or other voids of a diameter larger than or equal to that of the challenge spores contained within the biological indicator housing assembly B. This seal prevents the challenge spores from escaping the assembly B around the membrane G.

The cap C extends over the biological indicator housing assembly B thereby protecting the membrane from direct exposure or contamination. The structure and parts of the biological indicator housing assembly B, the cap C, and the media housing D are more clearly shown in FIGS. 2A, 2B, 2C, and 2D.

The preferred embodiment of the cap C is shown in detail in FIGS. 2 and 2A. The cap C includes an inverted receptacle 22 with a base wall 24 and an approximately conical side wall 26. The conical side wall 26 extends downward and outward from the base toward the media housing. The conical side wall 26 is substantially circular in cross section such that a cross sectional cut nearer the base is of a smaller diameter than a cross sectional cut further away from the base. The base wall 24 defines a fluid opening or hole 28 for fluid passage extending from an inner surface 30 to the environment via cap C.

Alternatively, cap C may be any body capable of enveloping or otherwise covering the biological indicator housing assembly B while allowing fluid access E to biological indicator housing assembly. One alternative embodiment of cap C has a cylindrical rather than conical shape.

Figure 3:
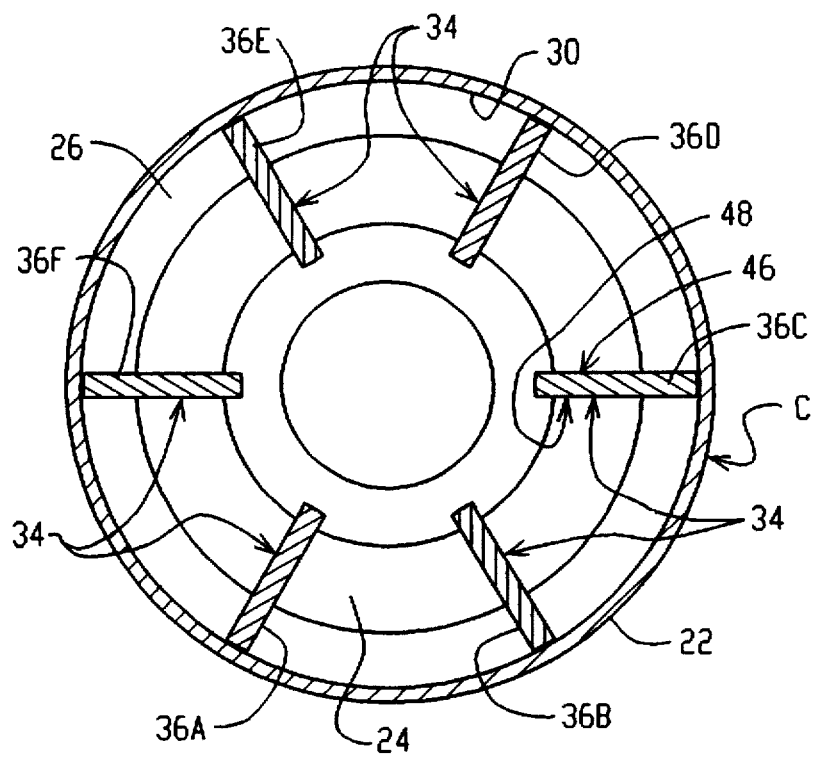
FIG. 3 is a sectional view taken through C of the preferred embodiment of the self contained biological indicator.
Figure 4:
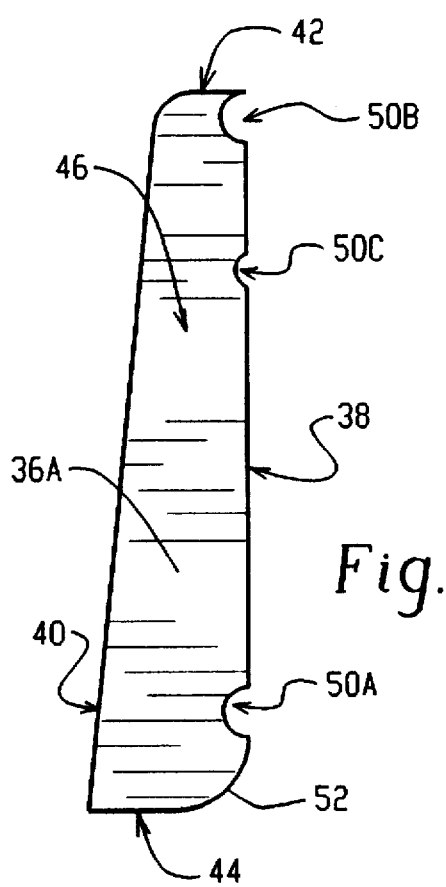
FIG. 4 is a side view of one of the fins in the preferred embodiment of the self contained biological indicator.

In one embodiment, cap C further includes a guide mechanism 34. The guide mechanism 34 snugly receives and guides the biological indicator housing assembly B within the cap C. The guide mechanism also allows for decontamination or sterilization and disinfecting, as well as rinse fluids to flow between cap C and media housing D. In the most preferred embodiment which is shown in more detail in FIGS. 3 and 4, the guide mechanism 34 includes six fins 36A, 36B, 36C, 36D, 36E, and 36F. Although six fins are shown, the guide mechanism 34 may be any of numerous other quantities and arrangements of fins would snugly receive and guide biological indicator housing assembly B equally well.

The preferred embodiment of each fin 36A-36F has a front edge 38, a back edge 40, a top edge 42, a bottom edge 44, and two sides 46 and 48. Each back edge is connected to both the base wall 24 and the circular side wall 26 on inner surface 30 of cap C. The front edge 38 is generally parallel to the biological indicator housing assembly B. In contrast, the back edge 40 is not generally parallel to either the front edge 38 or the biological indicator housing assembly B, but is instead parallel to the inner surface 30 along which the back edge 40 is connected.

The preferred embodiment of each fin 36A-36F also includes three notches or detents 50A, 50B, and 50C, and a rounded corner 52 between each front edge 38 and the bottom edge 44. Alternatively, these detents may be any means for engaging lips as described below where the detents securely hold the lips in place while still allowing movement of the lips within the open area 54 between the fins 36A-36F when movement of the cap C relative to the media housing D occurs. The detent 50A is the closest detent to the rounded corner 52 and the bottom edge 44. The detent 50A is sized to receive a flange 56 on the media housing D as described below in more detail. The detent 50B is the furthest detent from the rounded corner 52 and the bottom edge 44. The detent 50B is sized to receive both the flange 56 on the media housing D and a rim 58 on biological indicator housing assembly B as is described in more detail below. The detent 50C is the detent in between the detents 50A and 50B. The detent 50C is sized to receive the rim 58 on the biological indicator housing assembly B.

The media housing D defines a holding compartment or reservoir for holding growth media F. In the preferred embodiment of media housing D shown in FIGS. 1 and 2B includes an open vial or container 60 with a base wall 62 and an approximately conical side wall 64. The conical side wall 64 extends upward and outward from the base toward the cap. The conical side wall 64 is substantially circular in cross section such that a cross sectional cut nearer the base is of a smaller diameter than a cross sectional cut further away from the base. The conical side wall 64 includes the flange 56 extending circumferentially outward from the open end opposite the base 62. The flange forms a lip that is engaged initially by the detent 50A prior to the sealing process as described below, and subsequently by the detent 50B upon completion of the sealing process.

The fluid opening 28, as shown in FIGS. 2 and 2A, extends from the inner surface 30 to the surrounding environment. This fluid opening defines one of the fluid passageways between the biological indicator housing system and the environment. The interaction between the cap C and the media housing D defines the other fluid passageway. This other fluid passageway is a donut-shaped opening 66 circumferentially around the outside of the conical side wall 64 of the media housing D in between the bottom edge 44 of each of the fins 36A-36F. These two fluid passageways define the fluid entrances and exits of the microbial decontaminant and the rinse media. These fluid entrances and exits define the beginning and ending portions of the tortuous path E, as specifically defined as 16. The access to the biological indicator stored within the biological indicator storage assembly B as defined by the tortuous path E makes external contamination less likely. At the same time, the combination of the biological indicator housing assembly B, the cap C, and the media housing D permits efficient entrance and exit of microbial decontamination fluid between the challenge spores and the surrounding environment.

The construction and positioning of biological indicator housing assembly B in reference to the cap C modifies the tortuous path E. The combination of the biological indicator housing assembly B, the cap C, and the media housing D form a mechanism that after a fluid microbial decontamination cycle is simultaneously sealed and immersed into a growth media F.

Figure 2C:
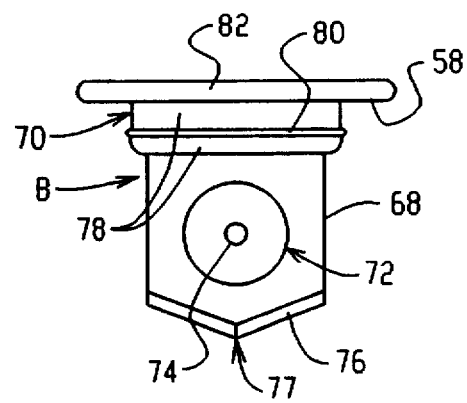
FIG. 2C is an exploded sectional view taken from the side of a preferred embodiment of the self contained biological indicator showing the dart with the microporous membrane removed.
Figure 5:
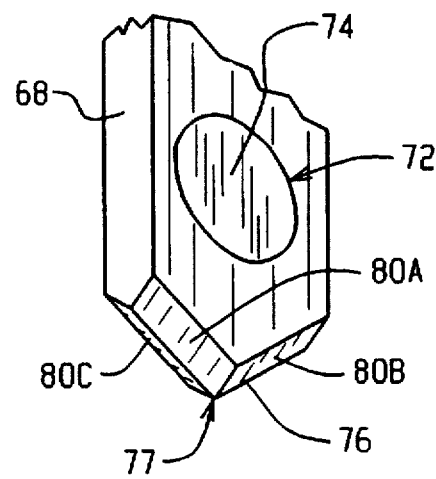
FIG. 5 is a perspective view of the cutting portion of the dart in the preferred embodiment where the dart is removed from the self contained biological indicator.
Figure 6:
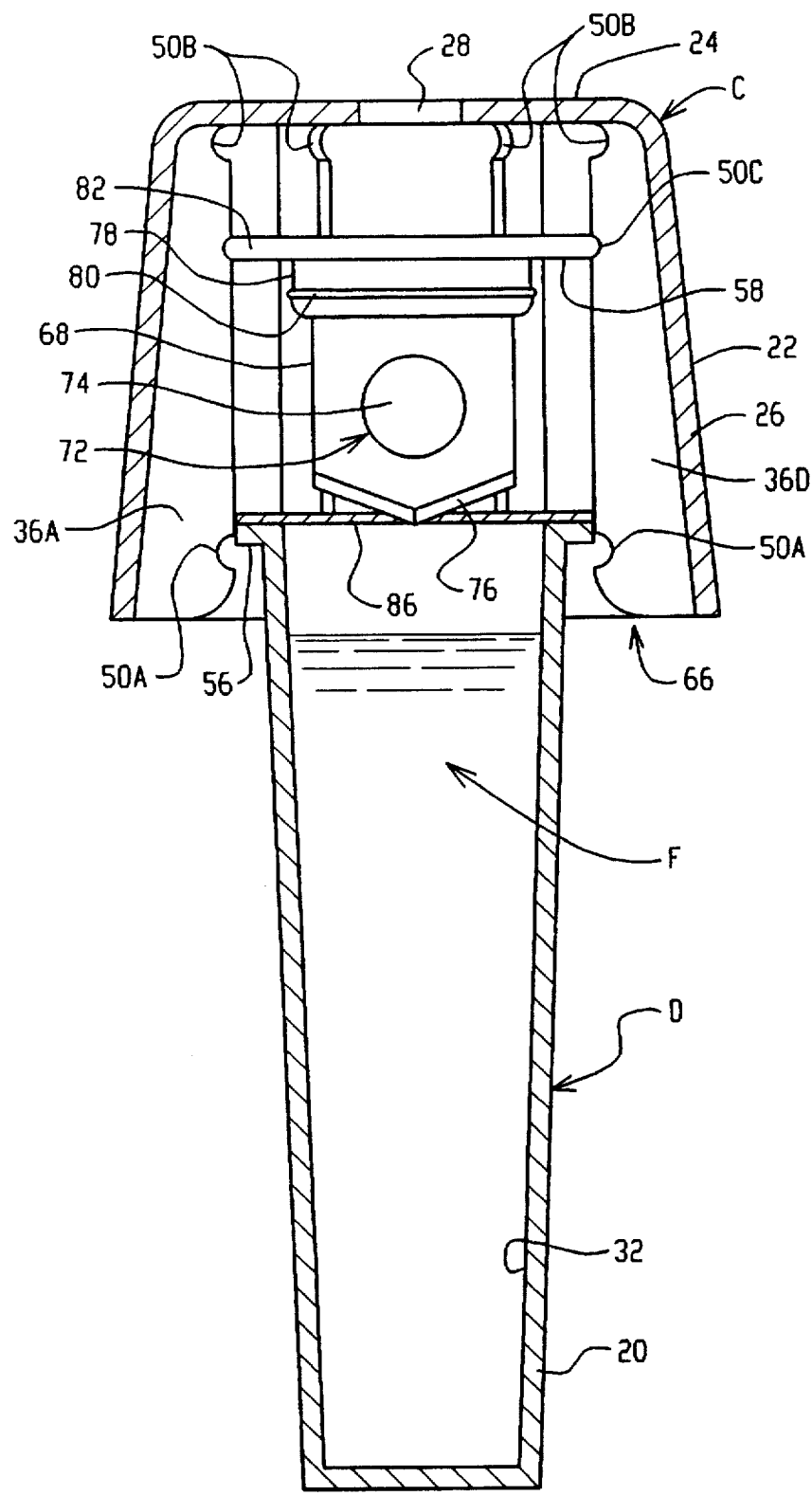
FIG. 6 is a sectional view taken from the side of a preferred embodiment of the self contained biological indicator with the self contained biological indicator in a second position.

In the preferred embodiment the biological indicator housing assembly B includes a dart 68 with a sealing plug 70 attached thereto as is shown in FIGS. 2 and 2C. The dart 68 further has a spore storage chamber 72 for receiving a carrier such as a paper disk 74 with challenge spores thereon which may be of any shape or dimension including rectangular as shown in FIG. 2 or circular as shown in FIG. 2C, and which may be suspended, affixed or otherwise positioned therein in any manner. The end of the dart 68 opposite the end having the sealing plug 70 attached thereto has a cutting edge 76. The preferred embodiment of the cutting edge 76 is shown in FIG. 5 where the cutting edge 76 has a center piercing point 77. Piercing point 77 is defined as the intersection of four cutting faces 80A, 80B, 80C, and 80D. Each of the cutting faces is beveled from its adjacent side of the dart 68 to its adjacent cutting face, i.e., for instance cutting face 80A is a beveled surface extending from the side of dart 68 with chamber 72 therein to both adjacent cutting faces 80B and 80C. The intersection of each of the cutting faces with an adjacent cutting face is a cutting edge where the intersection of all of the cutting edges is the piercing point 77. This piercing point 77 extends outward from the dart 68 further than the cutting faces and edges.

The sealing plug 70 of the dart 68 has a sealing base 78 with a sealing bead 80 thereon, and a sealing top 82. The base 78 and top 82 define the external rim 58 extending out from the base 78. The external rim 58 interacts with detents 50A–50C, preferably only detents 50B–50C, during the various processes of assembling, sterilizing, rinsing, sealing and immersing, and checking.

Figure 7:
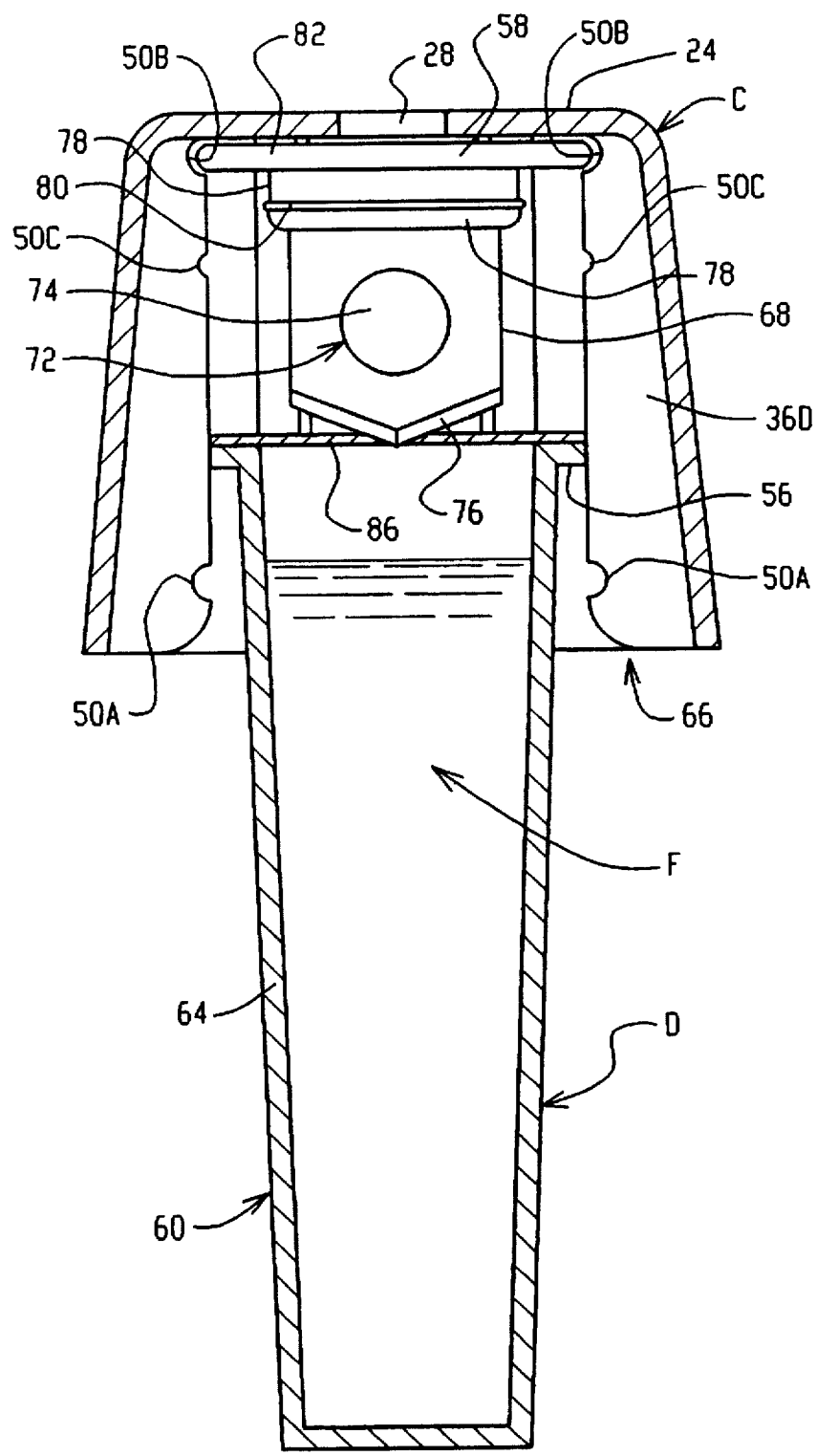
FIG. 7 is a sectional view taken from the side of a preferred embodiment of the self contained biological indicator with the self contained biological indicator in a third position.

Prior to assembly of self contained biological indicator A, the paper disk 74 with challenge spores thereon is positioned in the chamber 72 and the vial 60 is filled with growth media F. Specifically, the paper disk 74 carrying the contamination challenging spores is inserted into the chamber 72. The chamber 72 is then covered by the microporous membrane G which is affixed to opposite sides of the dart 68 as described above. This seals the challenge spores into the chamber 72 by preventing the spores from escaping around the microporous membrane. The vial 60 is filled with the growth media F and sealed by seal 86 that is a foil seal in one embodiment. Specifically, the foil 86 is sealed over the flange 56 on the vial 60 where the vial contains the growth media F. In the most preferred embodiment, the foil 86 is a lamination of aluminum foil and polypropylene, and the media vial 60 is molded using polypropylene. The foil 86 is heat sealed onto the flange 56 thereby fusing the polypropylene of the foil 86 and the vial 60. The biological indicator housing assembly B (dart 68), the cap C, and the media housing D (vial 60) are now ready for assembly.

The assembly of self contained biological indicator A involves inserting both the dart 68 and the vial 60 into the cap C. Specifically, the vial 60 is substantially filled with growth media F and a foil seal 86 is sealed around the flange 56. The dart 68 is inserted up into the open area 54 of the cap C until the flange 56 engages the detents 50C of each fin 36A–36F. The dart is now suspended in the cap C. The vial 60 is then inserted into the open area 54 typically until the flange 56 engages detents 50A of each fin 36A–36F. The vial 60 is typically not inserted any further because further insertion will result in the cutting edge 76 of the dart 68 touching and then cutting the foil seal 86 sealing the growth media in the vial 60. With the rim 58 of the dart 68, and the flange 56 of the vial 60 properly inserted into detents the 50C and 50A, respectively, the self contained biological indicator A is ready for decontamination, sterilization or disinfection.

To determine spore viability, the entire self contained biological indicator A including the paper disk 74 carrying the contamination challenge spores is decontaminated using microbial decontamination fluid. The dart 68 is then sealed in the vial 60. The sealing process immerses the paper disk 74 carrying the contamination challenge spores in the dart 68 into the growth media F. The self contained biological indicator A is incubated to accelerate any spore growth. Sealing of dart 68 in vial 60 avoids evaporation of growth media F in addition to providing a seal against stray microbes. If spores grow, then decontamination of the contamination challenge spores was not successful and thus decontamination items in the same or recent processes is not assured.

In more detail, microbial decontamination occurs when the self contained biological indicator A is in a first position as is shown in FIGS. 1 and 2. The design of the cap C with six fins 36A–36F permits gaseous or liquid microbial decontamination (microbial decontamination media such as fluid sterilant) to freely enter and exit the cap C. The exchange of fluids within the cap is further facilitated by fluid opening 28 at the top of the cap C. The microbial decontamination fluid enters and exits by either or both open area 54 and fluid opening 28. The microbial decontamination fluid may be any fluid capable of both passing through the microbial membrane G and of destroying all or selected biological and/or chemical substances.

In the preferred embodiment, the self contained biological indicator A is immersed into the microbial decontamination fluid where the fluid enters into the inside of the cap C by way of the open area 54, i.e., the open space between fins 36A–36F and the vial 60, and/or the fluid opening 28. Conversely, air exits the inside of the cap C by the opposite route as the microbial decontamination fluid entrance. Once within the cap C, the microbial decontamination fluid acts on the spores on the paper disk 74 contained within the dart 68.

After the microbial decontamination fluid has thoroughly flowed through the self contained biological indicator A and particularly dart 68, the microbial decontamination fluid is often rinsed out of the processor. Rinsing typically involves subjecting the self contained biological indicator A in a bath of microbe-free water. The water replaces the microbial decontamination fluid and rinses the contents of the self contained biological indicator A. Through the same liquid path, the rinse water will replace the microbial decontamination fluid within the cap C.

Upon draining of the rinse water via the same fluid path within the cap C, all the liquid will exit and air will replace it. The dart 68 and the sealing plug 70 remain contaminant-free when introduced into the growth media F to avoid a false, contamination indication. Both the dart 68 and the sealing plug 70 are protected from inadvertent external contamination by the tortuous path E. The entrance/exit path permitted by the fluid opening 28 to the dart 68 and the sealing plug 70 is interrupted by rim 58. Similarly, the path through the open area 54, i.e., around the fins 36A–36F between the cap C and the media vial 60 requires a right angle to access the dart 68 and the sealing plug 70 and thus is also tortuous. In each case, improper handling will not contaminate the dart 68 and the sealing plug 70.

The dart 68 has the cutting edge 76 to facilitate puncturing of the media sealing foil 86. To utilize the self contained biological indicator A after exposure to the decontamination process, the cap C is manually depressed to activate the system. Upon depressing of the cap C, the dart 68 will engage the foil 86 as indicator A moves into a second position as is shown in FIG. 6. Specifically, flange 56 of vial 60 leaves detents 50A thereby moving indicator A into a second position as is shown in FIG. 6.

The steps after the dart engages the foil which result in the dart seating in the housing may occur in one of two ways depending upon the system tolerances. In either case, the puncturing of the foil 86 will begin and, through continued downward motion, rim 58 of the sealing plug 70 is dislodged from detents 50C and ultimately lodges in detents 50B as is shown in FIG. 8. Sealing plug 70 engages media vial 60 and fit within in a sealable fashion within the opening at the flange end 56 of the vial.

In one embodiment as is shown in FIG. 7, after cutting edge 76 engages foil 86, where the foil is of sufficient puncture-resistance that it does not fully puncture prior to the housing D fully seating within cap C, thereby prohibiting dart 68 from seating fully within housing D, then the indicator slips into a third position as is shown in FIG. 7. Specifically, external rim 58 on sealing plug 70 is pushed out of or otherwise slips from its initial detents 50C to its final detents 50B before flange 56 of vial 60 slips from its initial detents 50A to its final detents 50B. This results in the positioning of the rim 58 within the cap C at a location that interrupts the path created by the fluid opening 28.

Figure 9:
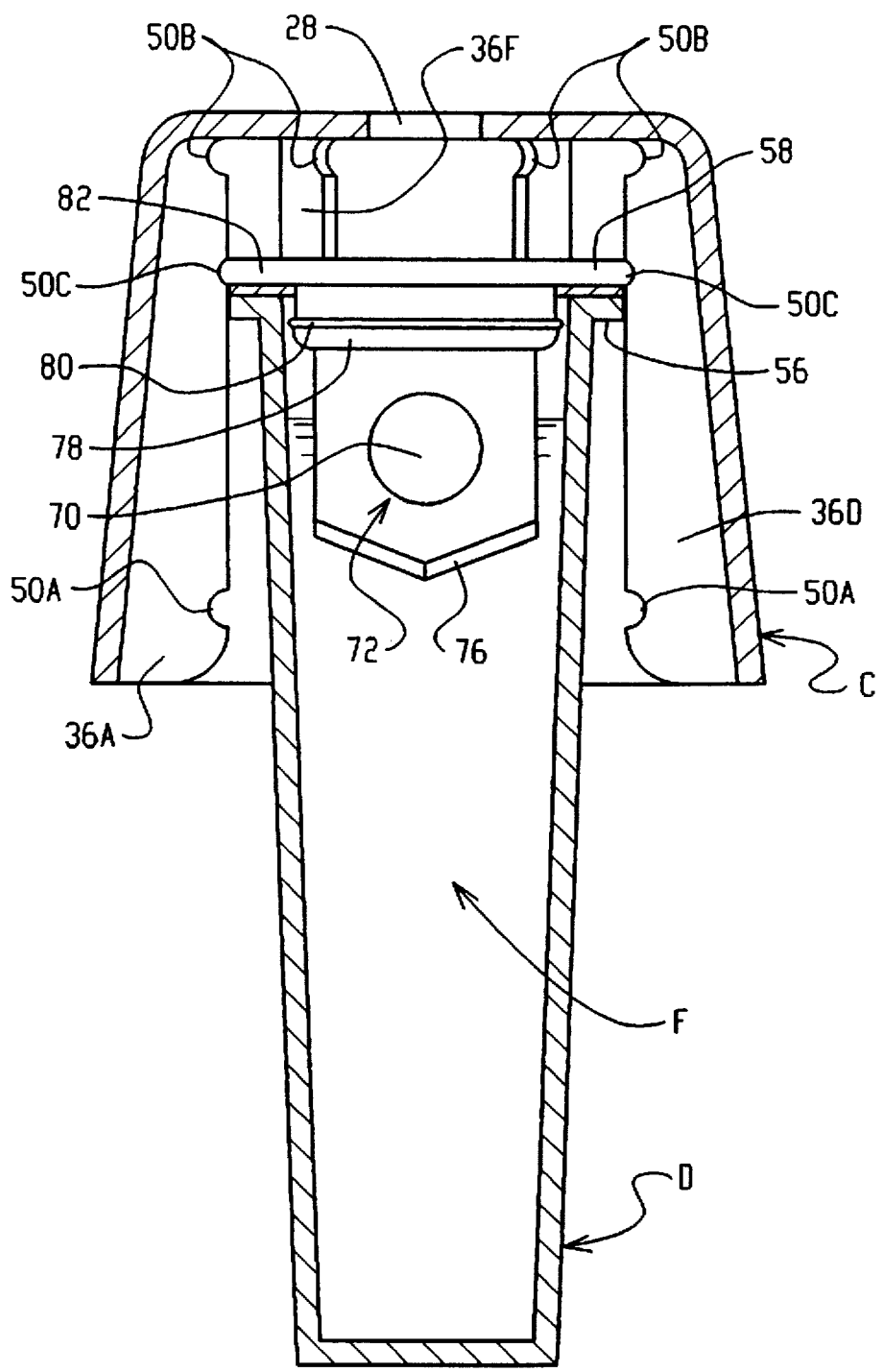
FIG. 9 is a sectional view taken from the side of a preferred embodiment of the self contained biological indicator with the self contained biological indicator in an alternative third position; and, FIG. 10 is a partial sectional view taken from the side of an alternative embodiment of the self contained biological indicator with the indicator connected in line.

Alternatively in a second embodiment as is shown in FIG. 9, where the foil is fully punctured prior to the housing D fully seating within cap C, thereby allowing dart 68 to fully seat within housing D, then the indicator slips into an alternative third position as is shown in FIG. 9. Specifically, the external rim 58 on sealing plug 70 may not position the rim 58 within the cap C at a location that interrupts the path created by the fluid opening 28 if the flange 56 of the vial 60 slips from its initial detents 50A to its final detents 50B before the rim 58 of the dart 68 slips from its initial detents 50C to its final detents 50B.

In yet a third alternative, the rim 58 of the dart 68 is pushed from its initial detents 50C to its final detents 50B while the flange 56 of the vial 60 slips from its initial detents 50A to its final detents 50B such that both move at different intervals and eventually rest in detents 50B at the same time.

Alternatively, other arrangements and methods are possible so long as after microbial contamination and rinsing, the cutting edge 76 pierces the foil 86 to expose growth media F either simultaneously or sequentially in a rather hurried manner with closing off of the tortuous path E.

Figure 8:
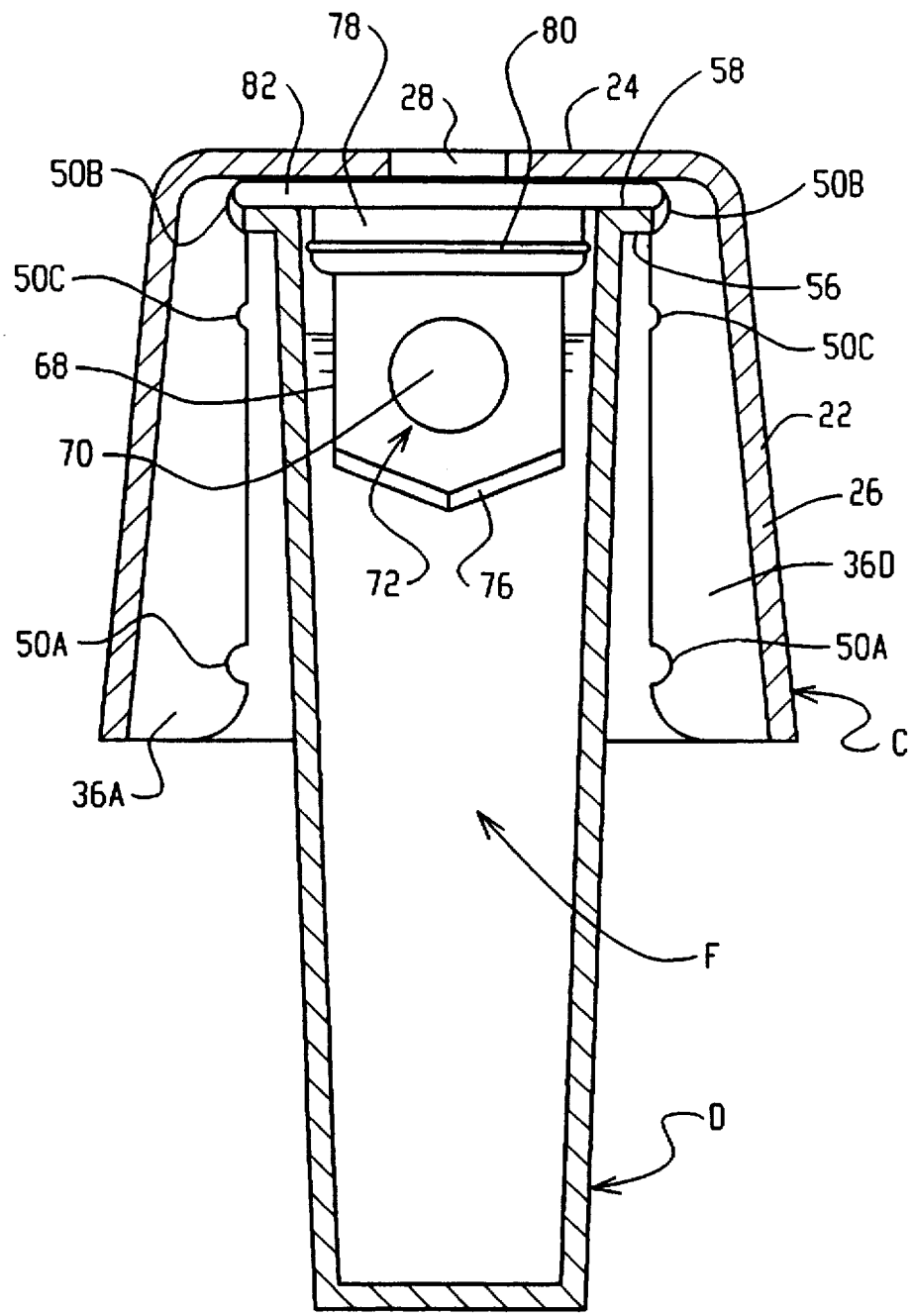
FIG. 8 is a sectional view taken from the side of a preferred embodiment of the self contained biological indicator with the self contained biological indicator in a fourth position.

In either case, the continued downward motion of cap C that substantially simultaneous ruptures the foil seal 86, closes off the tortuous path E as is shown in FIG. 8 which is the fourth and final position of indicator A. This continued downward motion also immerses the dart 68 into vial 60 containing the growth media F as is also shown in FIG. 8. This immersion causes the paper disk 74 carrying the contamination challenging spores within the chamber 72 of the dart 68 to interact with the growth media F. Basically, the spore disk contained within dart 68 is introduced into the growth media F resulting in the testing of the decontamination process. The sealing bead 80 of the sealing plug 70 provides a formable high pressure seal through its dimensional interference. Upon full closure, the sealing plug rim 58 is stopped by the media vial flange 56 where both are now in detents 50B. The sectioned pieces of the foil cut by the dart 60 lie within the media vial 68.

The self contained biological indicator is typically now incubated to determine spore viability. Sealing of the dart 68 within the vial 60 avoids evaporation of growth media F during incubation up to seven days. During incubation, any viable spores grow. Their growth releases byproducts into the culture medium. The byproducts can be detected, e.g., by a pH change, a pH changed induced color change, an opacity change and the like, to determine if any challenge spores survived the microbial decontamination process. The microbial membranes G covers the chamber 72 and tightly seals the perimeter of chamber 72 to the dart 68 via seal 14. The membranes prevents turbidity, i.e. suspension of the spores in the culture medium thereby causing the medium to become milky by prohibiting the spores from passing through the membranes. Eliminating the turbidity facilitates machine and human monitoring for color and opacity changes.

Figure 10:
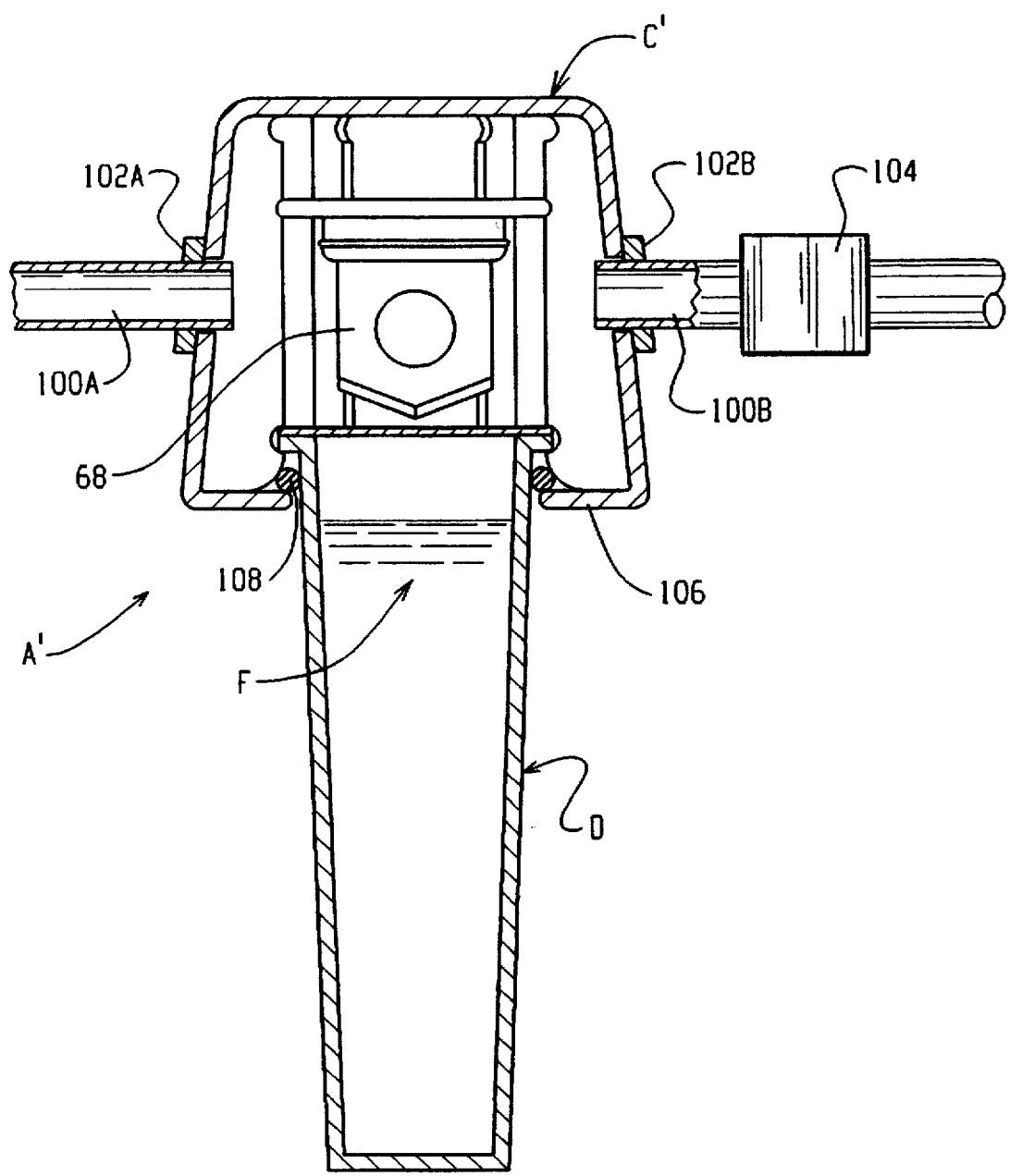

With reference to FIG. 10, some microbially decontaminated instruments have internal passages. To assure microbial decontamination of the interior passages, the antimicrobial fluid is pumped or circulated through the interior passages. This subjects the interior and exterior of the items to different microbial decontamination conditions. To assure microbial decontamination of the interior passages, a sealed biological indicator A is connected by tubing 100A, 100B with the interior passage anti-microbial fluid flow. The indicator A' is fluidly attached to fluid supply tubing 100A and 100B via connectors 102A and 102B on the cap C'. Connectors 102A and 102B may be any type of connector capable of connecting in a sealed manner a tube-like structure such as tubing 100A and 100B to the cap C'. The cap C' is substantially similar to the cap C in the preferred embodiment except that the fluid passageway 28 in the base 24 is either capped or nonexistent, and the donut-shaped opening 66 circumferentially around the outside of conical side 64 of media housing D in between the bottom edge 44 of each of the fins 36A–36F is covered substantially by the face 106. In addition, a seal seals the face 106 to the conical side wall 64.

Self contained biological indicator A' further has a restrictor 104 in one of the tubings 102A or 102B for restricting flow through the indicator A' so as to mimic closely the pressure and flow patterns through the lumens or other elongated fluid passageways in the equipment to be microbially decontaminated. The restrictor 104 may be any fluid flow restriction device such as a valve in which fluid flow can be adjustably controlled.

The invention has been described with reference to the preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is claimed:

1. A method of determining effectiveness of a microbial decontamination process, the method comprising:
    trapping a plurality of challenge microorganisms within a chamber, the chamber being permeable to a decontamination fluid such that the fluid comes into contact with the microorganisms;
    passing a microbial decontamination fluid used in the microbial decontamination process into the chamber holding the plurality of challenge microorganisms;
    lodging the chamber in a first set of detents in a cap and lodging a vial in a second set of detents in the cap, the vial containing a growth medium;
    dislodging the chamber and the vial in any order from their respective detents in the cap;
    lodging the chamber and vial together in a third set of detents in the cap such that the microorganism vial is opened and the chamber and the microorganisms are immersed in the growth medium; and,
    monitoring the growth medium to determine if the microorganisms grow.

2. A self-contained biological indicator system for indicating the effectiveness of a decontamination fluid, the self-contained indicator system comprising:
    a biological indicator storage assembly having a microorganism storage chamber for holding live challenge microorganisms;
    a media housing for holding a growth media supporting the growth of any live challenge microorganisms introduced into the growth media by the biological indicator storage assembly;
    a cap having a cavity therein for holding the biological indicator storage assembly and for selectively receiving the media housing, the cap including a plurality of fins, each fin including a plurality of detents, the plurality of detents including a rim engaging detent for engaging a rim on the biological indicator storage assembly, a flange engaging detent for engaging a flange on the media housing, and a combination receiving detent for engaging both the rim and the flange when the rim and flange are brought into contact; and, a microporous membrane covering the microorganism storage chamber in the biological indicator storage assembly, the membrane having pores which are sufficiently small that the challenge microorganisms are trapped in the microorganisms storage chamber of the biological indicator storage assembly while being sufficiently large that microbial decontamination fluid passes through.

3. The self contained biological indicator system as set forth in claim 2 wherein the membrane is hydrophilic.

4. The self contained biological indicator system as set forth in claim 3 wherein the membrane is selected from the group consisting of polyethylene, polypropylene, acrylic copolymers, polysulfone, polyethersulfone, ethylene vinyl alcohol, polyacrylonitrile, polycarbonate, polyphthalate carbonate, nylon and cellulosics.

5. The self contained biological indicator system as set forth in claim 2 further including a paper disk encapsulated within the microorganism storage chamber and supporting the challenge microorganisms.

6. The self contained biological indicator system as set forth in claim 2 wherein the cap and the media housing define a tortuous path between the microporous membrane and the ambient environment surrounding the self contained biological indicator system.

7. A self-contained biological indicator system for indicating the effectiveness of a decontamination fluid, the self-contained indicator system comprising:

a media housing for holding a growth media supporting the growth of any live challenge microorganisms introduced into the growth media, the media housing including an opening covered by a frangible seal;

a dart having a first end and a second end, the first end having a cutting edge for severing the frangible seal, the dart having two opposite surfaces which converge to form the cutting edge of the dart, the dart further having an aperture extending between the two opposite surfaces, challenge microorganisms being received in the aperture, a micro porous membrane being connected with the two opposite surfaces covering the aperture at opposite ends for receiving the challenge microorganisms, the micro porous membrane having pores which are sufficiently small that the challenge microorganisms are trapped in the aperture while being sufficiently large that the microbial decontamination fluid passes through; and, a cap having a cavity therein for holding the dart and for selectively receiving the media housing.

8. The self-contained biological indicator system as set forth in claim 7 wherein the second end of the dart includes a seal therearound for sealing the media housing during the immersion of the challenge microorganisms in the growth media and sealing the microorganisms into the media housing.

9. In a self-contained biological indicator system having a culture medium housing closed by a frangible seal, challenge microorganisms disposed adjacent the frangible seal, and a cap defining an open region adjacent the challenge microorganisms, the cap being mounted to the culture medium housing for movement at least between (i) a first orientation for permitting microbial decontamination fluids to flow into the open region and contact the challenge microorganisms and flow out of the open region and (ii) a second orientation in which the frangible seal is broken and the challenge microorganisms are introduced into the culture medium, the improvement comprising:

a cutting dart mounted at one end to the cap and having a cutting edge at a second end thereof, the cutting edge being disposed adjacent the frangible seal in the first orientation and moving through the seal and into the culture medium as the cap moves from the first orientation to the second orientation, the dart including two flat surfaces, the surfaces defining a bore therebetween within which challenge microorganisms are received.

10. A self-contained biological indicator system for indicating the effectiveness of a decontamination fluid, the self-contained biological indicator system comprising:

a vial for holding a growth medium for supporting the growth of any inoculate microorganisms introduced into the growth medium;

a chamber for trapping a plurality of challenge microorganisms, the chamber being permeable to a decontamination fluid such that the fluid comes into contact with the microorganisms;

a cap defining a cavity therein said cap having a guide mechanism including a first set of detents for lodging the chamber, a second set of detents for lodging the vial and a third set of detents for receiving the chamber and the vial from the first and second sets of detents, said third set of detents being arranged such that the vial, when received in the third set of detents, is opened and can receive the chamber and its contents;

a dart supported by the cap having an upper disc with a sealing flange therearound and a cutting blade extending downward from the upper disc, the cutting blade defining the challenge microorganism storage chamber therein for holding challenge microorganisms; and said guide mechanism for selectively connecting the cap to the vial such that the dart is movable between a first position with the challenge microorganism storage chamber suspended in the cap cavity and a second position with the dart upper disk and sealing flange sealing the vial and the challenge microorganisms immersed in the growth medium.

11. The self contained biological indicator system in claim 10 wherein the guide mechanism includes:

a plurality of fins attached in the interior cavity of the cap, each fin having the plurality of detents thereon; and, a flange on the medium housing slidably engaged by the fins.

12. The self-contained biological indicator system as set forth in claim 10 wherein the cap and the medium housing engage in a fluid tight relationship and further including:

a fluid inlet defined in the cap and a fluid outlet defined in the cap;

a tube connected with the fluid inlet for carrying a flow of microbial decontamination fluid into the cavity; and, a flow restrictor for regulating the microbial decontamination through the cap cavity.

13. A self-contained biological indicator system for indicating the effectiveness of a decontamination fluid, the self-contained biological indicator system comprising:

a medium housing for holding a growth medium for supporting the growth of any inoculate microorganisms introduced into the growth medium;

a cap defining a cavity therein;

a dart supported by the cap and having a challenge microorganisms storage chamber which holds challenge microorganisms; and, a guide mechanism for selectively connecting the cap to the medium housing such that the dart is movable between a first position with the challenge microorganism storage chamber suspended in the cap cavity and a second position with the dart sealing the medium housing, and the challenge microorganisms immersed in the growth medium, the guide mechanism including a plurality of fins attached in the interior of the cap, each fin having a plurality of detents thereon, the plurality of detents including a rib engaging detent for engaging a rib on the dart when the dart is in the first position, a flange engaging detent for engaging a flange on the medium housing, and a combination detent for engaging both the rib and the flange when the dart is in the second position.

14. A self-contained biological indicator comprising:

a tube for carrying an incoming flow of microbial decontamination fluid;

a cap defining an interior cavity for receiving the incoming microbial decontamination fluid, the cap being connected with the tube, the cap defining a fluid outlet that permits the microbial decontamination fluid to flow through and out of the cavity;

a flow restrictor for controlling the rate at which the microbial decontamination fluid flows through the cavity;

challenge microorganisms disposed in the cavity such that the microbial decontamination fluid flows over the challenge microorganisms;

a reservoir of culture medium separated from the challenge microorganisms by a frangible seal;

a microporous membrane enclosing the challenge microorganisms to prevent the challenge microorganisms from being entrained in and carried away by the microbial decontamination fluid flow while permitting the microbial decontamination fluid and the culture medium to permeate the membrane and the challenge microorganisms;

a cutting mechanism for selectively breaking the frangible seal; and, a guide mechanism for moving the challenge microorganisms into the media housing to immerse the challenge microorganisms in the culture medium.

* * * * *

UNITED STATES PATENT AND TRADEMARK OFFICE
CERTIFICATE OF CORRRECTION

PATENT NO. : 5,736,355  
DATED : April 7, 1998  
INVENTOR(S) : Dyke et al.

Page 1 of 2

It is certified that error appears in the above-identified patent and that said Letters Patent is hereby corrected as shown below:

On the title page, add the following item [56]

U. S. PATENT DOCUMENTS

| EXAMINER INITIAL | | PATENT NUMBER | | | | | | | ISSUE DATE | PATENTEE | CLASS | SUBCLASS | FILING DATE IF APPROPRIATE |
|---|---|---|---|---|---|---|---|---|---|---|---|---|---|
| | | 4 | 4 | 1 | 6 | 9 | 8 | 4 | 11/22/83 | Wheeler, Jr. | | | |
| | | 3 | 6 | 6 | 1 | 7 | 1 | 7 | 05/09/72 | Nelson | | | |
| | | | | | | | | | | | | | |

UNITED STATES PATENT AND TRADEMARK OFFICE
CERTIFICATE OF CORRRECTION

PATENT NO. : 5,736,355
DATED : April 7, 1998
INVENTOR(S) : Dyke et al.

It is certified that error appears in the above-identified patent and that said Letters Patent is hereby corrected as shown below:

FOREIGN PATENT DOCUMENTS

| | | DOCUMENT NUMBER | | | | | | PUBLICATION DATE | COUNTRY OR PATENT OFFICE | CLASS | SUBCLASS | TRANSLATION YES | NO |
|---|---|---|---|---|---|---|---|---|---|---|---|---|---|
| | | DE | 20 | 2 | 7 | 6 | 0 | 4 | 02/1971 | Germany | | | | |
| | | DE | 90 | 0 | 3 | 2 | 5 | 5 | 05/1990 | Germany | | | | |
| | | GB | 2 | 18 | 69 | 7 | 4 | A | 08/1987 | U.K. | | | | |
| | | | | | | | | | | | | | | |

Attest:

Signed and Sealed this

Sixth Day of April, 1999

Q. TODD DICKINSON

*Attesting Officer*   Acting Commissioner of Patents and Trademarks